United States Patent [19]
Minuth

[11] Patent Number: 5,316,945
[45] Date of Patent: May 31, 1994

[54] CELL CARRIER ARRANGEMENT

[76] Inventor: Will Minuth, Starenstrabe 2, 8403 Bad Abbach, Fed. Rep. of Germany

[21] Appl. No.: 989,840

[22] Filed: Dec. 14, 1992

[30] Foreign Application Priority Data

Dec. 14, 1991 [DE] Fed. Rep. of Germany ....... 4141295
Jan. 10, 1992 [DE] Fed. Rep. of Germany ....... 4200446

[51] Int. Cl.$^5$ ............................................. C12M 1/10
[52] U.S. Cl. .................................... 435/285; 435/284; 435/310; 435/312; 210/615; 210/619
[58] Field of Search ............... 435/284, 285, 310, 312; 210/615, 619

[56] References Cited

U.S. PATENT DOCUMENTS

| | | | |
|---|---|---|---|
| 3,812,016 | 5/1974 | Muller | 435/312 |
| 3,839,155 | 10/1974 | McAleer et al. | 435/312 |
| 3,925,165 | 12/1975 | Muller | 435/312 |
| 4,004,981 | 1/1977 | Hurni et al. | 435/312 |
| 4,310,630 | 1/1982 | Girard et al. | 435/284 |
| 4,600,694 | 7/1986 | Clyde | 435/312 |
| 4,789,634 | 12/1988 | Muller-Lierheim | 435/288 |
| 4,999,302 | 3/1991 | Kahler et al. | 435/266 |
| 5,139,953 | 8/1992 | Honda et al. | 435/312 |

FOREIGN PATENT DOCUMENTS 3932633  4/1991  Fed. Rep. of Germany .

OTHER PUBLICATIONS

Chem.-Ing.-Tech. 52 (1980), No. 12, p. 952, picture 1.11.

Primary Examiner—James C. Housel
Assistant Examiner—N. Bhat
Attorney, Agent, or Firm—Hoffman, Wasson & Gitler

[57] ABSTRACT

A cell carrier arrangement for cultivating adhering cells having at least two blanks connected with one another. The blanks are separated by a gap and are made of flat material, wherein at least one of the blanks is produced from a material which is permeable for a respective treatment medium of cells.

8 Claims, 4 Drawing Sheets

CELL CARRIER ARRANGEMENT

BACKGROUND OF THE INVENTION

The invention relates to a cell carrier arrangement for cultivating adhering cells.

There is already known, for example, a reactor for performing biological in vitro processes in which a carrier shaft is placed rotatably in a cylindrical reactor vessel (DE-OS 39 32 633). This carrier shaft possesses several disk-like holding sieves attached to it, each of which are filled with a bead polymerizate, which serves as carrier for cell cultures. This known reactor has an expensive design. In addition, real or natural conditions for the growing of cell cultures are not assured.

The object of the present invention is to provide a cell carrier arrangement which is suitable in an optimal way for treatment, especially also cultivation, of biomaterial, and especially of cells, as well as also for observation and recording of the behavior of cells, as well as for the production of biomass.

To achieve this object, a cell carrier arrangement including at least two blanks connected with one another, which between them form at least one gap or gap-like area and are a flat material, and at least one of the two blanks is produced from a material which is permeable for a respective treatment medium for the cells.

SUMMARY OF THE INVENTION

The cell carrier arrangement according to the invention consists in the simplest case of a single double-layer cell carrier. At least one of the two layers is produced from a material which is permeable to the respective treatment medium. "Treatment medium" in the meaning of the invention is a gaseous, but preferably liquid medium with which the respective cell culture is treated and/or is supplied on the cell carrier arrangement. But "treatment medium" in the meaning of the invention can also be a medium which contains substances such as (biomatter) produced by the biomaterial (cell culture).

By suitable selection of the material and/or by suitable coating, the permeability can be matched and/or also selected to the respective application so that by the wall or membrane formed by the blank, only a passage of quite specific, selected substances of a treatment medium exhibiting a combination of substances is possible.

Already in its simplest design as a double-layer cell carrier, the cell arrangement according to the invention not only has the advantage that this cell carrier makes possible an exchange of substances for the cells of the cell culture adhering to a wall or to a blank through this wall, but the cell carrier arrangement also allows for a high cell density in a small amount of treatment medium.

In an embodiment of the invention, the double-layer cell carriers formed by the blanks are each provided stacklike on a holder. This embodiment has the advantage that on the cell carriers, respectively different cell populations can be provided, which are separated by the membranes, but can interact through these membranes and by their interaction produce the desired biological result.

The cell carrier arrangement according to the invention is suitable, for example, also for the production of cell modules for medical uses (by using organ-specific adhering cells), specifically for the use or for the support of natural organs. Further, the cell carrier arrangement according to the invention is suitable also as bioreactor or for the use in bioreactor applications, especially also for mass production of biomatter.

BRIEF DESCRIPTION OF THE DRAWINGS

The invention is explained in more detail below based on the figures. There are shown in.

DETAILED DESCRIPTION OF THE INVENTION

Figure 1:
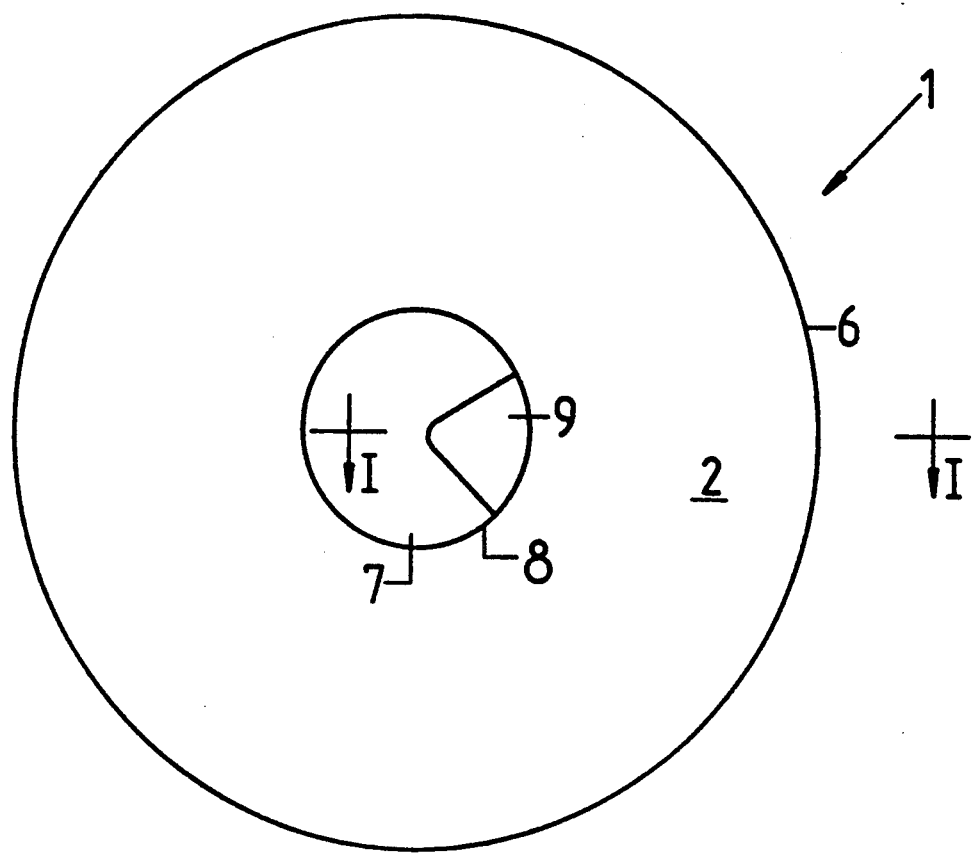
FIG. 1 is a diagrammatic representation and top view of a cell carrier arrangement in the form of a double-walled or double-layer cell carrier according to the invention.
Figure 2:
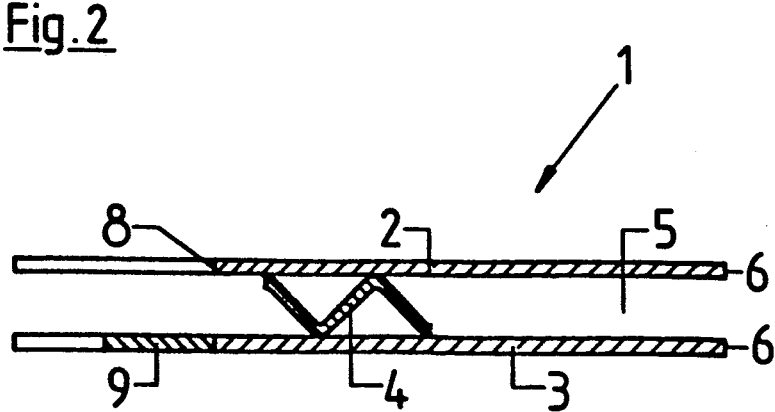
FIG. 2 is a section corresponding to lien I—I of FIG. 1.

In FIGS. 1 and 2, 1 is a cell carrier, which basically consists of two circular disk-like blanks 2 and 3 in the represented embodiment. In the represented embodiment, both blanks 2 and 3 consist of a permeable material and thus form permeable membranes. The materials for blanks 2 and 3 are selected corresponding to the respective application, specifically, for example, so that the membranes formed by blanks 2 and 3 make possible a molecular exchange or passage of air, gas, liquids, especially treatment and growth media, etc., in only one direction or in both directions. A blank, for example, lower blank 3 in FIG. 2, can also be produced from an impermeable material. Further, different materials can be selected for the blanks so that blank 2 is permeable for other substances than blank 3.

Both blanks 2 and 3 are held parallel and at a distance from one another by a fabric or a lattice 4, specifically so that between these blanks, a space or gap 5 is produced, which is most permeable from periphery 6 of cell carrier 1, on which both blanks 2 and 3 lie with their edges coinciding, up to a center opening 7 of cell carrier 1. Opening 7 is formed by punching a suitable opening in both blanks 2 and 3. On edge 8 of opening 7, both blanks 2 and 3 are again placed basically coinciding, but blank 3 exhibits a nose-shaped extension 9 projecting inward over edge 8 into opening 7 and in the area of edge 8 exhibits approximately a width which corresponds to an angle length of somewhat less than 90°.

Instead of fabric or lattice 4, other means can also be used to hold both blanks 2 and 3 at a distance from one another. Thus, it is possible, for example, that the material used for blanks 2 and 3 exhibits embossings or projections or is provided with such, and then these embossings and projections hold blanks 2 and 3 at a distance from each other. Other techniques are also conceivable.

Cell carrier is used in the simplest case, for example, for cultivating, observing, etc., cells or cell cultures in a culture dish 10. For this purpose, blank 2 then is used, for example, with its outside as base of substrate on which the cells adhering there are increased. In gap 5, gaseous or liquid media, for example, liquid nutrients or growth media, are introduced in substances to be examined, etc., with suitable means (pipettes, etc.) and especially the introduction of liquid media is substantially facilitated by projection 9 projecting into opening 7. The advantage of cell carrier 1 is, for example, also that for the cells adhering to blank 2, a substance exchange is possible by this blank 2, by which, for example, the growth and/or also the behavior of the cells are improved.

Figure 3:
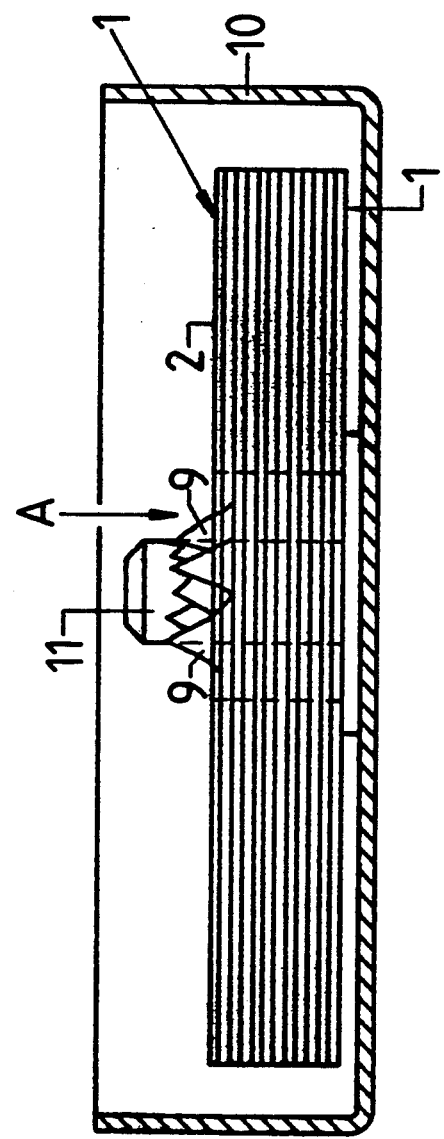
FIG. 3 is a diagrammatic representation of a cell carrier arrangement consisting of several cell carriers in a Petri or culture dish.
Figure 4:
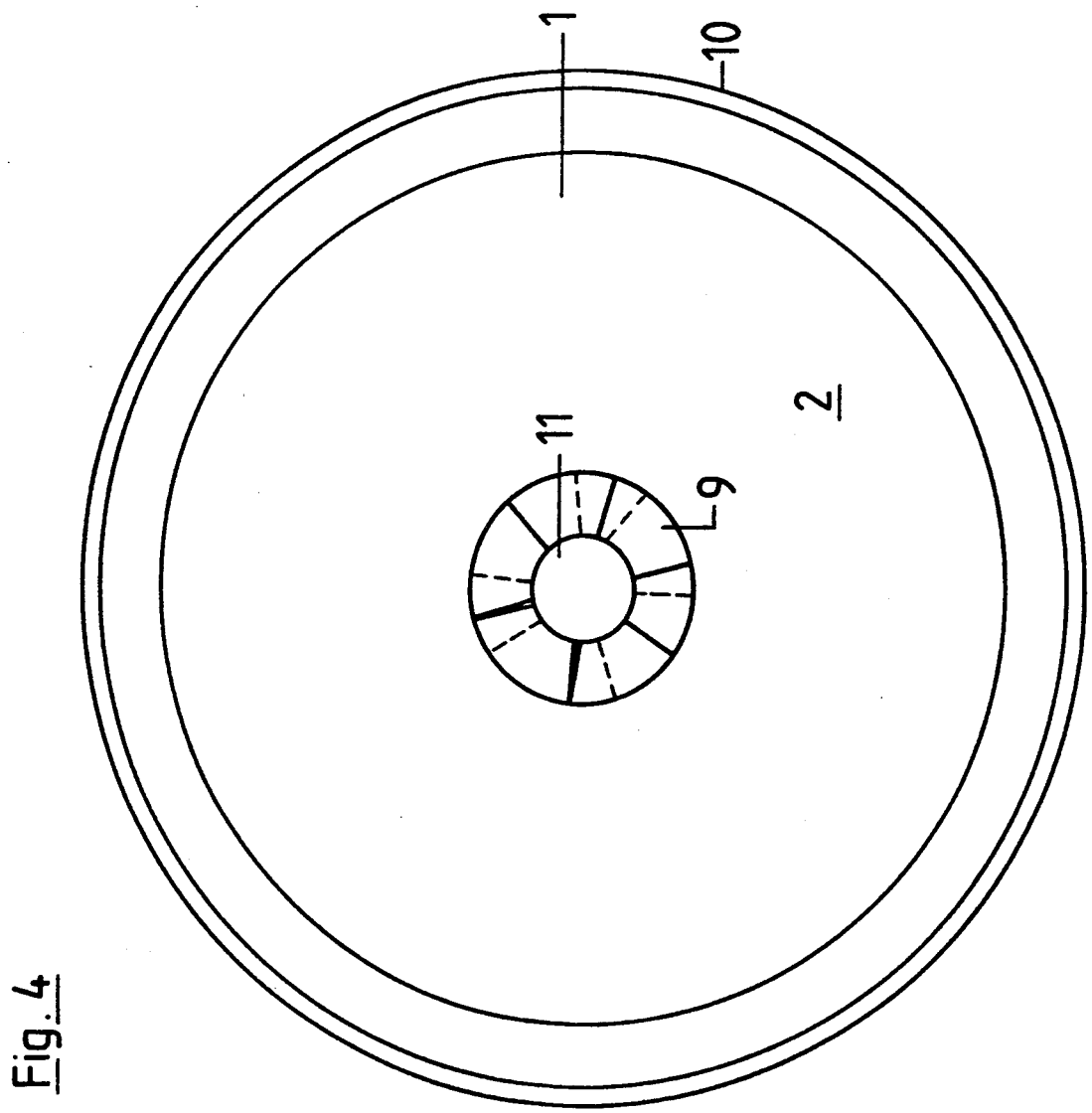
FIG. 4 is a top view of FIG. 3.

FIG. 3 shows an arrangement, in which several cell carriers 1 are stacked on top of one another in culture vessel 10. In this case cell carriers 1 are slid on or slipped on a holding pin 11 placed standing in culture dish 10, holding pin whose outside diameter is somewhat smaller than the diameter of openings 7, specifically so that each projection 9 rests against the peripheral area of holding pin 11 running obliquely upward from edge 8 and projections 9 of cell carrier 1 are provided uniformly distributed around the axis of holding pin 10, so that these projections 8 form a structure shaped like a neweled staircase around holding pin 11 and thus liquid medium introduced from above into the gap between holding pin 11 and edge 8 of cell carrier 1 corresponding to arrow A by projections 9 also reaches gap 5 of each cell carrier 1.

The cultivation of cells takes place here again on the outside surface of a blank, for example, on the top side of blank 2, and thus on the top side of topmost cell carrier 1 as well as below it respectively in the area between two successive cell carriers 1 in a stack. It is thus possible to cultivate respectively similar cells or else cells of different type to achieve, for example, a deliberate influencing of different cells. This can be necessary, e.g., in the cultivation of cells which only grow in interaction or form a specific output.

Figure 5:
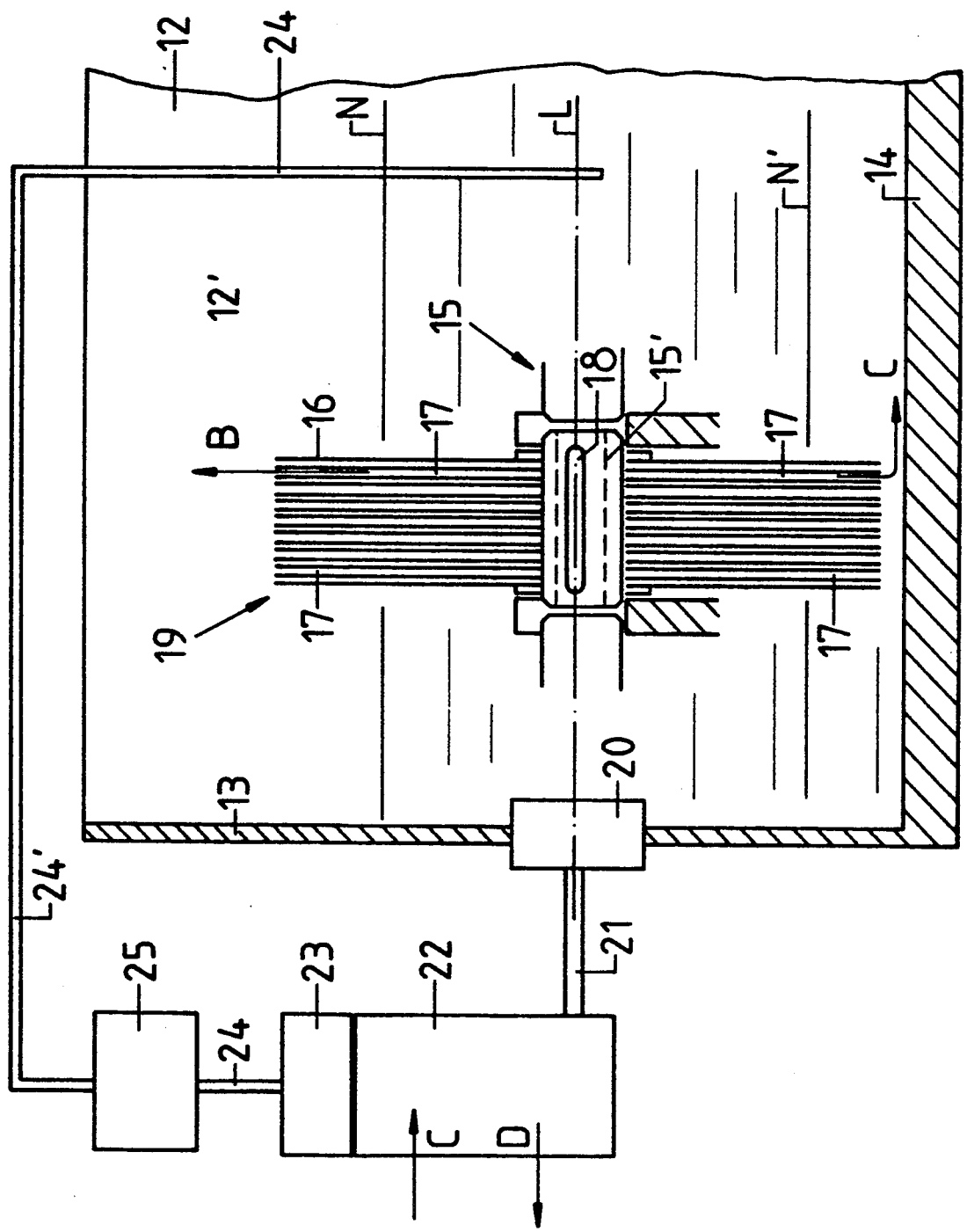
FIG. 5 is a simplified and diagrammatic representation of a bioreactor with a cell carrier arrangement consisting of several cell carriers.

FIG. 5 shows a bioreactor in simplified representation. In the represented embodiment it consists of a parallelepiped-shaped housing 12 with a sealed peripheral wall 13 and a sealed bottom 14, which, for example, is heatable. A hollow shaft 15 is mounted rotatably around its horizontal longitudinal axis L running parallel to bottom 14 an inner space 12' of housing 12 open on its top side and which can be closed there preferably by a cover, not shown. Shaft 15 consists of several short sections 15', which are connected with one another, at least with respect to drive, to shaft 15 and each of which carries a plurality of blanks 16, which are produced in the same way as blanks 2 and 3 again from the permeable material.

Circular disk-like blanks 16 each have the same size, are placed with their axis coaxial with the axis of section 15' and are attached in a suitable way to respective section 15', so that blanks 16 are corotated when section 15' or rotating shaft 15 rotated. Blanks 16 continue to be at a distance from one another so that between these blanks 16, areas for growing or cultivating cells as well as also areas 17 lying between them are produced for the passage of a treatment medium, for example, a liquid nutrient. Each section 15' is provided with a continuous slot 18 extending in axial direction, by which said medium can enter from inside hollow shaft 15 or sleevelike section 15' into areas 17.

Blanks 16 or membranes each provided on sections 15' form wheel-like structures or cell carrier arrangements 19.

By a drive not represented in more detail, shaft 15 or sections 15' connected with one another to this shaft and wheel-like cell carrier arrangements 19 provided there are driven slowly rotating around the axis of hollow shaft 15.

During the operation, inner space 12' of housing 12 is filled with the liquid medium up to a desired level N so that the axis of shaft 15 lies below this level and dislike blanks 16 or cell carrier arrangements 19 project only with their upper partial area from the treatment liquid.

Hollow shaft 15 is closed on its one end. A pipe 21 is connected to the other end of hollow shaft 15 by a rotating joint 20, pipe which leads to the output of an exchanger 22. The input of exchanger 22 is connected with a pump 25 by a filter 23 to a pipe 24. With the help of pump 25, treatment medium can be conveyed from inner space 12' through pipe 24 to filter 23 and by the latter to the input of exchanger 22. Filter 23 is especially designed so that it retains cells, which optionally are co-conveyed together with the treatment liquid through pipe 24.

The dense, lamellar arrangement of blanks 16, achieves that the treatment liquid in areas 17 in each case rises by capillary action, as this is indicated in FIG. 5 with arrow B, i.e., in this respect an extremely cell-protective, gentle flow of the treatment liquid occurs in the cells adhering to blanks 16. Because structures 19 are not completely immersed in the treatment liquid, a drawing along of this liquid from areas 17 and thus a conveying action, with which the treatment liquid is moved through these areas 17 also gently and above all also protective of the cells, is produced with the rotation of shaft 15 at the point where the periphery of each cell carrier arrangement 19 emerges from the treatment liquid by the surface tension of the treatment liquid. Of course, the rotation of shaft 15 also provides for all parts of blanks 16 or of cell carrier arrangement 19 and thus all areas of the adhering cell cultures to be treated or supplied uniformly with the treatment liquid, and by the vertical arrangement of blanks 16, which, moreover, are for the most part taken up in the treatment liquid, mechanical force effects impairing the growth of the cell cultures are avoided.

By exchanger 22, gaseous but also liquid substances can be added to the treatment liquid, but also to reactor space 12' (arrow C). Further, it is also possible conversely to remove gaseous or liquid substances from the treatment liquid by exchanger 22 (arrow D). Both possibilities can also be provided combined.

The bioreactor is suitable, for example, for the biological production of substances (biomass), but also, for example, for biological purification of gases or liquids, e.g., in a suitable design for hemodialysis. It is understood that the cells adhering to blanks 16 are correspondingly selected in their type in the respective application. In using the reactor for hemodialysis, these cells are then organ-specific cells, i.e., liver or kidney cells.

In the same way as blanks 2 and 3, blanks 16 of structure 19 preferably form double-layer cell carriers each, which then in each case are provided repeatedly next to one another on each section 15'. But other designs are also conceivable.

The invention was described above by embodiments. It is understood that numerous modifications are possible, without as a result leaving the inventive idea supporting the invention.

Thus, it is possible, for example, by using a two-layer cell carrier corresponding to cell carrier 1 and by using organ-specific cells adhering to the outside surfaces of the blanks or membranes, to produce a cell module for animal or human-medical applications, which is used, for example, as an implant for the support or the replacement of endogenous organs.

In the above description of FIG. 5, the assumption was that the level of the treatment medium in housing 12 lies at a level N, which is above axis L, so that only a relatively small part of each structure or cell carrier arrangement 19 projects from the treatment medium.

This design already also has, for example, the advantage that the air or gas exchange does not have to take place by the culture or treatment medium but can take place by the membranes or blanks 16, specifically where these blanks 16 or cell carrier arrangements 19 project from the treatment medium.

This advantage is especially achieved when only very little culture medium is used in inner space 12′, for example, the level of the culture medium lies, for example, at level N′, which is below axis L. In this case, the treatment liquid or the culture medium then flows into areas 17 formed between the membranes starting from hollow shaft 15 essentially downward. Here, too, again, this gentle and cell-protective flow of the treatment liquids caused by the small axial width of areas 17, with rotation of shaft 15 is supported in that at the point where each cell carrier arrangement 19 emerges from the treatment liquid, a drawing along of this liquid from area 17 and thus a conveying action is produced by the surface tension of the treatment liquid.

By the feeding of the treatment liquid by high shaft 15, a very low level N′ and thus a very small amount of treatment liquid is possible, with the advantage that with a very high portion of cells, only a small portion of treatment medium is necessary, in contrast to other known bioreactors.

What is claimed is:

1. A double-walled cell carrier arrangement for cultivating adhering cells, comprising a housing and at least two flat blanks connected with one another in a stacked manner on a holder and which between them form at least one gap or slot area, wherein at least one of the two blanks is produced from a material which is permeable to a respective treatment medium for said cells and the holder is a shaft or section of shaft disposed within said housing, and wherein said shaft or section of shaft is mounted rotatably around a horizontal longitudinal axis of the shaft or section of the shaft and has an opening therein connecting the gap area to a source of liquid treatment medium through an inner space of said shaft for feeding the liquid treatment medium to the gap area, and wherein the inner space is filled up to a level with the treatment medium so that the cell carrier arrangement projects the treatment medium.

2. A cell carrier arrangement according to claim 1, wherein the gap or slot area is formed by a spacer.

3. A cell carrier arrangement according to claim 2, wherein the spacer is formed by a lattice, gate, seam or fabric.

4. A cell carrier arrangement according to claim 1, wherein at least one blank is integrally formed with a flap projecting over an inner or outer edge of said blank.

5. A cell carrier arrangement according to claim 1, wherein said blanks are connected with one another in a stack in each case in pairs to a double-layer cell carrier.

6. A cell carrier arrangement according to claim 1, wherein said shaft is a hollow shaft or said section is a sleeved element.

7. A cell carrier arrangement according to claim 6, wherein a pipe connected to the inner space of said shaft or said section is provided to feed the treatment medium to the slot or gap area formed between said blanks.

8. A cell carrier arrangement according to claim 7, wherein the treatment medium is fed to said pipe by a filter or an exchanger, by which gaseous or liquid substances can be added to or removed from the treatment medium.

* * * * *